United States Patent [19]

Prionas

[11] Patent Number: 4,776,334
[45] Date of Patent: Oct. 11, 1988

[54] CATHETER FOR TREATMENT OF TUMORS
[75] Inventor: Stavros D. Prionas, Stanford, Calif.
[73] Assignee: Stanford University, Stanford, Calif.
[21] Appl. No.: 21,387
[22] Filed: Mar. 3, 1987

Related U.S. Application Data

[63] Continuation of Ser. No. 715,238, Mar. 22, 1985, abandoned.

[51] Int. Cl.[4] ............................................. A61B 17/36
[52] U.S. Cl. ................................................. 128/303.1
[58] Field of Search .................... 128/303.1, 395–398, 128/784, 786, 736, 738, 804

[56] References Cited

U.S. PATENT DOCUMENTS

| | | |
|---|---|---|
| 4,292,960 | 10/1981 | Paglione . |
| 4,392,040 | 4/1983 | Rand et al. . |
| 4,397,314 | 8/1983 | Vaguine . |
| 4,442,846 | 4/1984 | Brighton et al. . |
| 4,458,677 | 7/1984 | McCorkle . |
| 4,493,564 | 1/1985 | Epstein . |
| 4,522,212 | 6/1985 | Gelinas et al. . |

*Primary Examiner*—Max Hindenburg
*Attorney, Agent, or Firm*—Flehr, Hohbach, Test, Albritton & Herbert

[57] ABSTRACT

A catheter for use in treating tumors is flexible and relatively small in diameter so that it can be inserted interstitially into the tumor mass. A conductor is provided about a length of the catheter and is electrically insulated except for a small length or small lengths thereof which are adapted to be received within the tumor volume. By connecting the conductor to a high frequency power source a heat producing current can be generated through the tumor tissue adjacent the exposed portions of the catheter to damage the tumor cells. One or more temperature sensing devices are included in the catheter and are located adjacent to the exposed conductor or conductors for monitoring the temperature of the adjacent tumor tissue. The signals from these devices, which are picked up from a connector at one end of the catheter, can then be used to control the current to the conductor or conductors so as to maintain the tumor volume at a constant and uniform desired temperature.

6 Claims, 3 Drawing Sheets

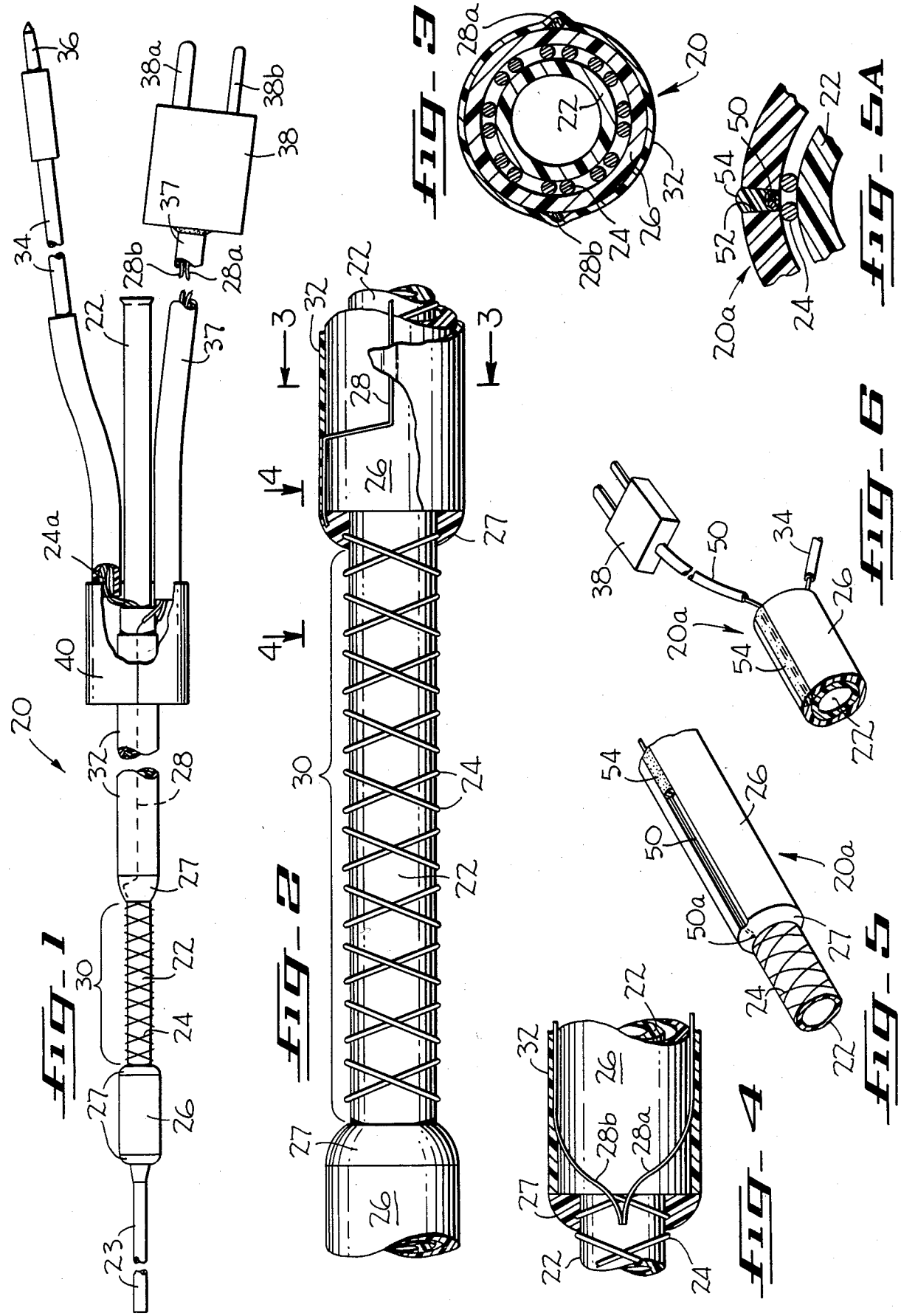

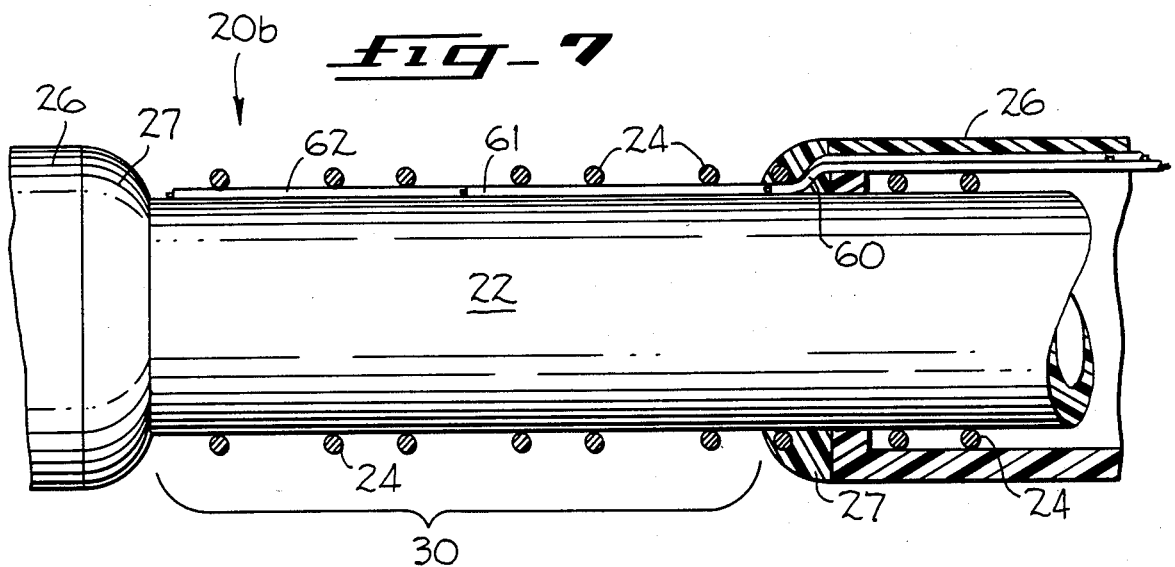
fig_7
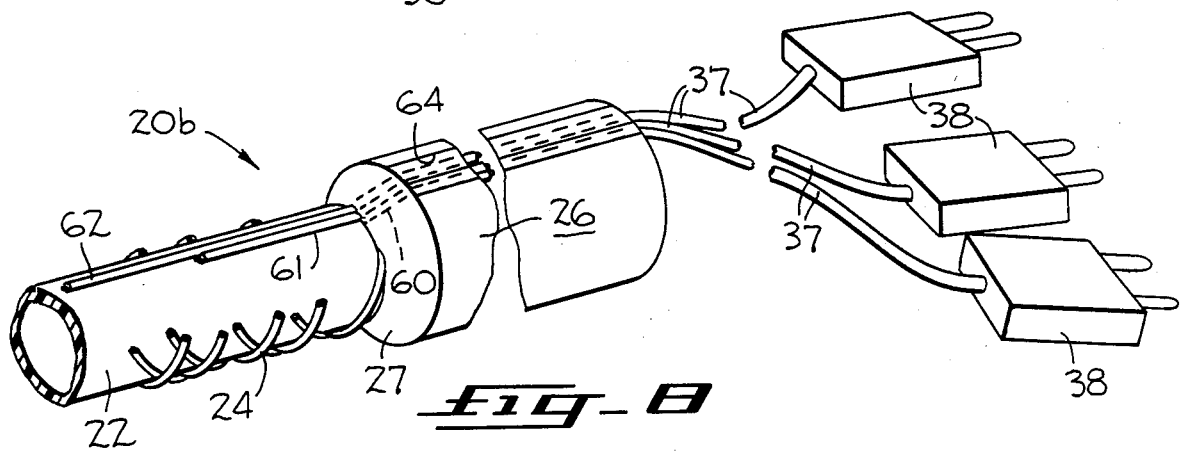
fig_8
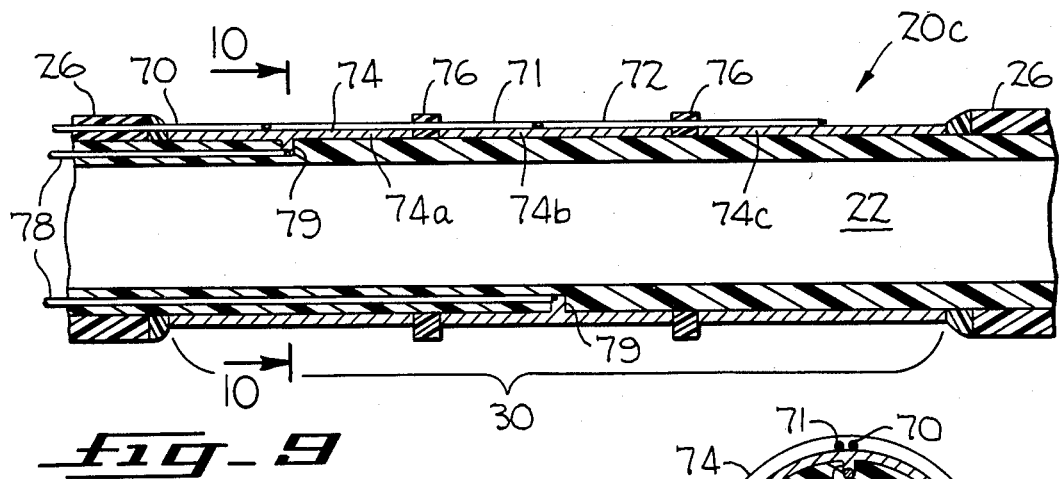
fig_9
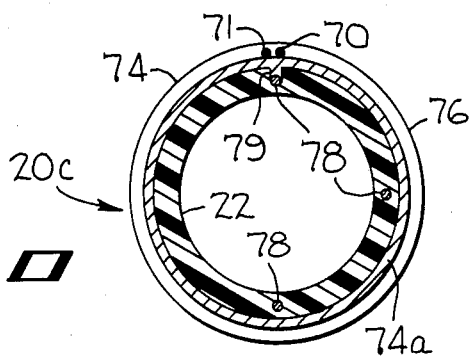
fig_10

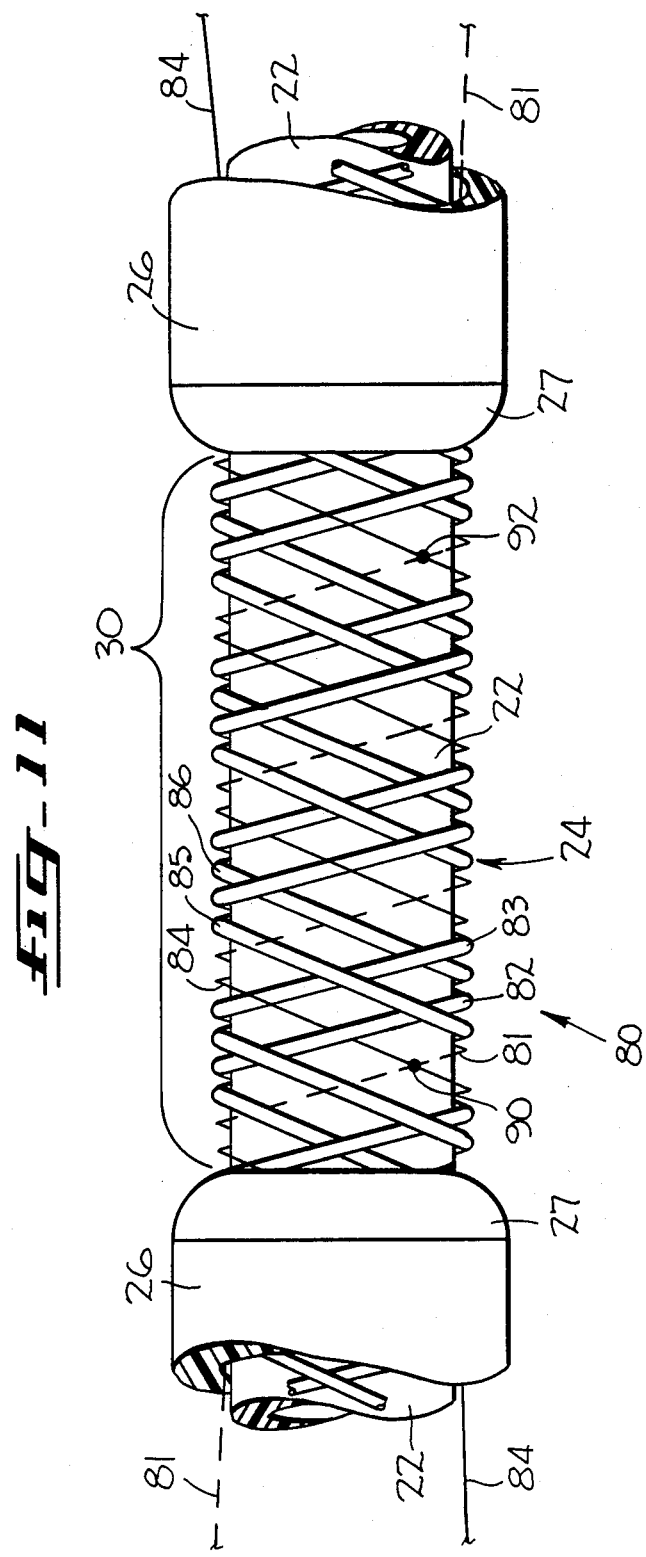
Fig_11

CATHETER FOR TREATMENT OF TUMORS

U.S. GOVERNMENT INTEREST

This invention was made with Government support under Grant Nos. CA4542 and CA19386 awarded by NCI/NIH. The Government has certain rights in this invention.

This is a continuation of application Ser. No. 715,238 filed Mar. 22, 1985 now abandoned.

BACKGROUND OF THE INVENTION

1. Field of the Invention

The present invention pertains to means for treating tumors, and particularly malignant tumors, in the bodies of animals, such as humans, and more particularly, it pertains to means which utilize the application of a controlled heat source to the tumor volume to cause or aid in the cause of its necrosis.

2. Description of the Prior Art

Recently, it has been proposed to provide a means for treating tumors which utilizes a flexible catheter that can be passed directly into or adjacent to the tumor volume. This has proven to be useful when the tumors are located well within the body of the patient so as not to be susceptible to surface hyperthermia treatment, and it has proven to be particularly useful when the tumor is located in a location which makes surgical removal difficult or impossible or particularly traumatic to the patient. The catheter comprises an inner tube of flexible plastic material having a central longitudinal passage therethrough. A conductive member is extended along the surface of the inner tube, and insulation is provided about the conductive member throughout the catheter except for a relatively small portion thereof which is arranged to be located adjacent to or within the tumor volume. The conductive member is connected to a high frequency power source so that a current can be passed from the exposed conductive member portion through the tumor to damage the tumor cells without significantly affecting the adjacent healthy tissue of the body. This invention is disclosed and claimed in U.S. patent application Ser. No. 565,505 of Don R. Goffinet, filed Dec. 27, 1983.

SUMMARY OF THE INVENTION

With the present invention, a catheter of the aforedescribed type is provided, i.e., a catheter comprising an elongate flexible supporting member of a size and flexibility adapting it to be interstitially implanted in the tumor volume of the patient even when the tumor is located well within the body of the patient in a generally inaccessible location. A conductor extends along at least a portion of the exterior circumferential surface of the supporting member and means are provided at one end of the catheter for connecting this conductor to a source of high frequency current. Insulation is provided about the conductor for a portion of the length thereof but another portion of the length of the catheter is free of insulation so as to expose the conductor. This exposed conductor portion of the catheter is arranged to be located directly adjacent to or within the malignant tumor tissue in the patient. Thus, when the high frequency current is switched on, current can be generated from the exposed conductor portion through the tumor tissue to cause necrosis of the same.

In accordance with the teachings of the present invention, a temperature sensing device is provided adjacent to the exposed conductor portion of the catheter, and some means (e.g., electrical, optical, etc.) is provided for the temperature sensing device extending along the catheter to one end thereof so as to provide a signal corresponding to the sensed temperature which signal can be delivered to an external source. Thus, by including temperature sensing means within the treatment portion of the catheter, control of the power delivered to the catheter can be achieved (by conventional feedback control means not relevant to the present invention), and the desired constant temperature within the malignancy may be maintained.

In alternative embodiments of the present invention, a number of temperature sensing devices may be provided adjacent to the exposed conductor portion to better achieve control, or alternatively, multiple exposed conductor portions may be provided, each being independently controlled and each having an independent temperature sensing device associated therewith.

BRIEF DESCRIPTION OF THE DRAWINGS

FIG. 1 is a side elevation of one embodiment of the catheter of the present invention with portions thereof being broken away and removed so that the different functional parts of the catheter can be shown in sufficiently large scale.

FIG. 2 is an enlarged side elevation, partially in section, of the catheter of FIG. 1 particularly illustrating the exposed conductor portion thereof.

FIG. 3 is an enlarged section taken on line 3—3 of FIG. 2.

FIG. 4 is a top plan partially in section taken in the direction of the arrows 4—4 of FIG. 2.

FIG. 5 is a partial isometric view, partially in section, of a second embodiment of the catheter of the present invention.

FIG. 5A is an enlarged transverse section through a portion of the catheter of FIG. 5 illustrating the positioning of the thermocouple wires on the catheter.

FIG. 6 is an isometric view of the end portion of the catheter of FIG. 5 and the connection elements thereof.

FIG. 7 is a longitudinal section through the exposed conductor portion of a third embodiment of the catheter of the present invention.

FIG. 8 is a partial isometric view of the catheter of FIG. 7.

FIG. 9 is a longitudinal section through a portion of a fourth embodiment of the catheter of the present invention.

FIG. 10 is an enlarged section taken on line 10—10 of FIG. 9.

FIG. 11 is a diagrammatic side elevation of a portion of a fifth embodiment of the catheter of the present invention.

DESCRIPTION OF THE PREFERRED EMBODIMENTS

As seen in FIG. 1, the catheter 20 of the present invention generally comprises a tubular supporting member 22 formed of a relatively hard, but flexible, plastic material. One end 23 of the supporting member 22 is reduced in diameter in order to permit the catheter to be threaded through a trocar for introduction into the interstitial tissues of a patient. Received tightly about the outer circumferential surface of the supporting member 22 is an open mesh conductor 24. A circumferential layer of insulation 26 tightly surrounds the conductor and is secured thereto by means of adhesive beads 27 so as to completely cover all of the conductor except for a preselected length 30 at a predetermined position along the length of the catheter. Thus, the conductor 24 is left exposed only in one relatively short section of the catheter wherein conduction of an electrical current through the tumor will occur. The length 30 of the conducting electrode portion of the conductor 24 will be sized to fit the size of the tumor to be treated. Catheters of the foregoing type are more fully and completely described in pending U.S. patent application Ser. No. 565,505 of Don R. Goffinet filed Dec. 27, 1983, and reference to such application may be had for a more full and complete description of such catheters and their method of use in performing various medical treatments.

In accordance with the teachings of the present invention, a temperature sensing device 28 is provided which, in the FIG. 1 embodiment, is comprised of a thermocouple formed of a pair of dissimilar wires 28a and 28b (FIG. 4) laid on top of the insulation 26. The ends of the wires 28a and 28b are joined together, as seen in FIG. 4, to form the thermocouple, such thermocouple junction being located within the adhesive bead 27 and just below the surface thereof (FIG. 2) so that it will be electrically insulated from the patient's tissue but close enough to be fully sensitive to the surrounding heat in the tissue. The thermocouple 28 is protected and electrically insulated by a very thin heat shrink tubing 32 which is secured about the insulation 26 extending from the conductive portion 30 of conductor 24 to the end of the catheter utilized for connection to the external power and control devices. As shown in FIG. 3, the heat shrink tubing 32 is relatively thin in diameter and tightly grips the outer circumference of the catheter.

At one end of the catheter, an unravelled and twisted together portion 24a (FIG. 1) of the mesh 24 is directed outwardly and joined to an insulated conductive member 34 which, in turn, is attached to a power connector plug 36. This connection, which permits the high frequency (R.F.) and high power electrical power supply to be connected to the exposed conductive portion 30 of conductor 24, is disclosed in further detail in the aforementioned U.S. patent application Ser. No. 565,505. As seen in FIG. 1, the thermocouple wires 28a and 28b are insulated and run through an insulating covering 37 to a connector 38 having prongs 38a and 38b for plug-in connection to conventional circuitry for sensing and measuring the voltage generated in the thermocouple and thereby determining the temperature of the patient's flesh at the conductive portion 30 of the catheter. A heat shrink tubing wrap 40 (FIG. 1) is provided about the connections to the external lead members 37 and 34 at the end of the catheter to insulate such connections.

While a thermocouple 28 has been specifically disclosed as the temperature sensing means, it will be readily apparent that other means of sensing temperatures and changes therein could be utilized in the catheter of the present invention such as, for example, thermistors, p-n junctions or fiberoptic probes.

By continuously sensing the temperature at the conductive portion 30 of the catheter, such temperature can be controlled by varying the power delivered to the conductor 24 through the power connector plug 36. Conventional feedback control means, not a part of the present invention, may be used to control the power delivered to the conductor 24 in accordance with the sensed temperature (e.g., by varying the input voltage) so that the desired temperature will be maintained within very narrow limits.

A second embodiment of the invention is disclosed in FIGS. 5, 6 and 5A. In the catheter 20a therein shown, the temperature sensing device 50 comprises an insulated pair of thermocouple wires with only the junction at the tip 50a being exposed and being positioned in the adhesive bead 27 as in the manner of the FIG. 2 embodiment to sense the temperature adjacent to the exposed portion 30 of conductor 24. The temperature sensor 50 extends from the exposed conductor along the length of the insulation 26 and is arranged to lie at the bottom of a groove 52 (FIG. 5A) cut lengthwise along the insulation. The groove is sealed and protected by a bead of adhesive 54 as shown. At the end (FIG. 6) of the catheter adapted to be connected to the external controlling instruments the thermocouple 50 extends outwardly from the body of the catheter and is suitably attached to a connector 38 as in the previously described embodiment. The conductor 24 is adapted to be connected to an external power source through extension 34 as previously described.

In order to improve the temperature controlling operation of the catheter, a plurality of temperature sensing devices can be utilized to sense the temperature at different positions along the exposed conductor portion 30 and thereby more reliably chart the actual temperature along the conductor (and hence across the tumor volume) to better control the tumor treatment operation by insuring that the tumor as a whole is at the required temperature. This may be accomplished, as shown in the embodiment of the invention illustrated in FIGS. 7 and 8, by providing a catheter 20b with three temperature sensor leads 60, 61 and 62 (which may be thermocouples or thermistors) all within a groove 64 (FIG. 8) extending longitudinally along insulation 26 of the catheter from one end thereof. The free ends of the temperature sensors are each connected to connector plugs 38 by means of insulated extensions 37 as in the previously described embodiments. At the conductive portion 30 of the catheter, the exposed ends of the temperature sensors are uniformly spaced apart so as to be located at each end and in the center of the conductive portion. In order to accomplish this, one sensor 60 terminates with its temperature sensitve tip located at one end of the conductive portion as with the previous embodiments. The second sensor 62 is extended across the conductive portion by being threaded beneath the conductive mesh 24 so as to lie directly adjacent to the inner supporting member 22 at the opposite end of the conductive portion. As shown in FIG. 7, the third sensor 61 terminates approximately in the center of the exposed conductive portion 30 and is threaded beneath the mesh 24 similarly to the sensor 62. By monitoring the temperature across the conductive portion, a better and more accurate control of the temperature of all portions of the tumor volume may be obtained.

As mentioned previously, the conductor 24 is formed of an open mesh. This will typically be formed by a special weave with a plurality of spaced wires being wound in a clockwise direction about the underlying supporting member 22 and a plurality of spaced wires being wound in a counterclockwise direction about the supporrting member 22. By constructing a thermocouple with certain of the wires during the weaving of the mesh 24, an alternative means of providing one or more temperature sensors across the exposed conductive portion 30 can be achieved. For example, if one of the plurality of wires wound in the clockwise direction is an insulated copper wire and if one of the plurality of wires wound in the counterclockwise direction is an insulated constantan wire, such wires can be connected together (e.g., by welding) at one of their crossings in the exposed conductive portion 30 of the catheter to form a thermocouple. The free ends of the copper and constantan wires can then be connected to connector plugs or the like for connection to conventional circuitry for sensing and measuring the temperature—as in the previously described embodiments. For providing a second temperature sensor in the exposed conductive portion, a second crossing of the constantan and a separate (i.e., second) copper wire can be welded together and the ends of the constantan and second copper wires at the end of the catheter used for connection to the temperature sensing circuitry.

An example of a catheter provided with temperature sensors in the conductive mesh 24 is shown somewhat diagrammatically in FIG. 11. The catheter 80, with the conductive portion 30 thereof being shown in FIG. 11, will be seen to be comprised of the supporting member 22, the outer insulation layer 26 and the conductive mesh 24 arranged as in the previously described embodiments. The mesh 24, as illustrated, is comprised of three separate wires 81, 82 and 83 wound in one direction (e.g., clockwise) about the supporting member 22 and three separate wires 84, 85 and 86 wound in the opposite direction (e.g., counterclockwise) about the cylindrical surface of supporting member 22. While wires 82, 83, 85 and 86 are the conventional conductors (e.g., nickel) carrying the high frequency electrical current which will pass through the tumor tissue from the exposed conductive portion 30, the wire 81 can be an insulated copper wire and the wire 84 can be an insulated constantan wire. These wires are then fused together so that there will be metal to metal contact at temperature sensing points 90 and 92 spaced apart across the conductive portion 30. Although not shown, it will be understood that the wires 81 and 84 are broken between points 90 and 92 to prevent any coupling between the thermocouples. The wires 81 and 84 at each end of the catheter can be separated from the remaining wires of the mesh and run through an insulated covering 37 to a connector 38 (not shown) as in the FIG. 1 embodiment of the invention.

It will also be apparent that a plurality of thermocouples of the aforedescribed type can be provided at the same end of the catheter by providing a separate copper (or constantan) lead for each thermocouple desired. Since a typical conductive mesh 24 would include about 6–8 separate wires wound in each direction, three separate thermocouples could be formed by using, for example, one constantan and three copper wires with the temperature sensing points being appropriately spaced across the conductive section 30 as in the FIG. 7 or FIG. 9 embodiments of the invention.

In order to further enhance the localized control of the temperature at discrete positions within the tumor volume and thereby assure greater uniformity of temperature throughout the tumor volume, I propose to provide a plurality of separate, independently driven exposed conductive portions 30 along a short portion of the catheter so that each may be independently powered and controlled separately from the others. Thus, rather than having a single electrode present on each catheter that is inserted into the tumor volume, a plurality of closely spaced electrodes can be provided to extend from one edge of the tumor to the other. In order to accomplish this, the embodiment of the invention shown in FIGS. 9 and 10 can be utilized. The catheter 20c partially shown therein includes an inner supporting member 22 and insulation 26 provided about the exterior surface thereof as with the previously described catheters. Three temperature sensors, 70, 71 and 72 are received in a longitudinally extending groove in the insulation so as to be located at uniformly spaced positions across the exposed conductive portion 30 of the catheter in generally the same manner as in the Figure 7 embodiment of the catheter. The conductive portion, however, is not formed by a mesh which extends to the end of the catheter but by spraying a conductive metallic material 74, such as silver, in a generally uniform depth between the ends of the insulation 26 defining the conductive portion of the catheter. A pair of insulating rings 76 are provided about the inner supporting member 22 at uniformly spaced positions within the exposed conductive portion 30 so as to divide such conductive portion into three separate conductors or electrodes 74a, 74b and 74c. In order to provide an independent power connection to each of the conductive electrodes 74a, 74b and 74c, longitudinal holes are provided in the wall of the tubing 22 so that conductive wires 78 can be extended therein. As can be seen from FIGS. 9 and 10, there are three holes accommodating the wires 78, and they are of different lengths so that they each extend to a position centered on the associated conductive electrode 74a–c. By means of pre-cut holes 79 connecting the ends of the longitudinal holes with the exterior surface of the supporting tubing 22, a conductive connection is made from the associated electrode 74a–c onto the associated conductive wire 78 during the time that the metallic material 74 is sprayed onto the supporting member 22. At one end of the catheter (not shown) the three separate wires 78 can be individually connected to separate power sources so that each electrode 74a, 74b and 74c can be separately powered as required in accordance with the temperatures sensed by the separate temperature sensing devices 70, 71 and 72, respectively.

Although the best modes contemplated for carrying out the present invention have been herein shown and described, it will be apparent that modification and variation may be made without departing from what is regarded to be the subject matter of the invention.

What is claimed is:

1. A catheter for use in treating tumors or the like within the body of a patient comprising an elongate flexible supporting member of a size and flexibility adapting it to be interstitially implanted in the patient, a plurality of conductors provided about said supporting member in spaced positions along a predetermined length of the supporting member adapted to correspond to the length of the catheter passage through the tumor to be treated, means for individually connecting each of said conductors to a source of high frequency current, electrical insulation extending about said supporting member over the length thereof and between said conductors to leave only said conductors exposed to permit conduction of current therefrom through the tissue of the patient, and means for separately sensing the temperature at each of said conductors and for providing signals indicative thereof whereby each of said conductors can be monitored and the power delivered thereto adjusted so as to provide a continuous uniform temperature through said tumor.

2. A catheter as set forth in claim 1 wherein said means for connecting comprises conductive leads embedded within said flexible supporting member and extending longitudinally thereof.

3. A catheter as set forth in claim 1 wherein said means for sensing comprises a plurality of temperature sensing elements positioned adjacent to said conductors and electrical leads extending from each of said elements along said insulation.

4. A catheter according to claim 1 wherein there are provided a plurality of said conductors arranged at longitudinally spaced positions along said catheter and a plurality of means for individually connecting the conductors to a source of high frequency current, said insulation serving to space said conductors from each other and from exposure for a predetermined distance from said one end of the catheter, and a plurality of said temperature sensing means for separately sensing the temperature of the tissue of the patient adjacent each exposed conductor portion.

5. A catheter for use in treating tumors or the like within the body of a patient, comprising:
an elongate supporting member adapted to be interstitially implanted in the patient, a plurality of conductive wires wound about the axis of the supporting member including one set of wires wound in one direction about the supporting member, and a second set of wires wound in the other direction, each set including at least two wires, at least one wire of each set being joined to one wire of the other to form a thermocouple,
temperature sensing means comprising at least one of the wires being joined to another of the wires at a temperature sensing position, the joined wires being made of different materials to form said thermocouple at their juncture,
and an insulating layer extending over the conductive wires for a portion of the length of the catheter, with another portion of the catheter being free of insulation to expose the wires and form a tumor heating portion, said thermocouple being associated with the tumor heating portion.

6. A catheter according to claim 5 wherein a plurality of thermocouples are formed across the exposed portion by joining selected wires from the first set to selected wires from the second set.

* * * * *